United States Patent
Stearns et al.

(10) Patent No.: US 7,470,255 B2
(45) Date of Patent: Dec. 30, 2008

(54) INTRODUCER ASSEMBLY WITH SUSPENDED SEAL

(75) Inventors: Ralph A. Stearns, Bozrah, CT (US); David C. Racenet, Litchfield, CT (US); Gene A. Stellon, Southington, CT (US)

(73) Assignee: Tyco Healthcare Group LP, North Haven, CT (US)

(*) Notice: Subject to any disclaimer, the term of this patent is extended or adjusted under 35 U.S.C. 154(b) by 281 days.

(21) Appl. No.: 11/184,323

(22) Filed: Jul. 19, 2005

(65) Prior Publication Data

US 2006/0041232 A1 Feb. 23, 2006

Related U.S. Application Data

(60) Provisional application No. 60/590,176, filed on Jul. 21, 2004.

(51) Int. Cl.
*A61M 5/178* (2006.01)

(52) U.S. Cl. ............... 604/167.06; 604/167.01; 604/167.03; 604/244; 604/513; 604/256; 604/272

(58) Field of Classification Search ............ 604/167.01, 604/167.03–167.04, 167.06, 244, 93.01, 604/513, 158–159, 164.01, 164.02, 171, 604/256, 272; 606/108; 251/149.1, 149.9; 137/872

See application file for complete search history.

(56) References Cited

U.S. PATENT DOCUMENTS

| 5,180,373 | A | 1/1993 | Green et al. |
|---|---|---|---|
| 5,197,955 | A | 3/1993 | Stephens et al. |
| 5,226,891 | A | 7/1993 | Bushatz et al. |
| 5,304,143 | A | 4/1994 | Green et al. |
| 5,324,270 | A | 6/1994 | Kayan et al. |
| 5,342,315 | A * | 8/1994 | Rowe et al. ............ 604/167.06 |
| 5,354,280 | A | 10/1994 | Haber et al. |
| 5,385,552 | A | 1/1995 | Haber et al. |
| 5,385,553 | A | 1/1995 | Hart et al. |
| 5,389,081 | A | 2/1995 | Castro |
| 5,407,433 | A | 4/1995 | Loomas |
| 5,411,483 | A | 5/1995 | Loomas et al. |
| 5,496,280 | A | 3/1996 | Vandenbroek et al. |
| 5,545,142 | A | 8/1996 | Stephens et al. |
| 5,549,565 | A | 8/1996 | Ryan et al. |
| 5,603,702 | A | 2/1997 | Smith et al. |
| 5,628,732 | A * | 5/1997 | Antoon et al. ......... 604/167.06 |
| 5,634,908 | A | 6/1997 | Loomas |
| 5,693,031 | A | 12/1997 | Ryan et al. |
| 5,709,664 | A | 1/1998 | Vandenbroek et al. |
| 5,720,759 | A | 2/1998 | Green et al. |
| 5,820,600 | A | 10/1998 | Carlson et al. |
| 5,827,228 | A | 10/1998 | Rowe |

(Continued)

*Primary Examiner*—Nicholas D Lucchesi
*Assistant Examiner*—Quynh-Nhu H Vu

(57) ABSTRACT

A surgical access apparatus includes an access member dimensioned for insertion within tissue and having a longitudinal opening to permit introduction of a surgical object through the access member to perform a procedure on underlying tissue. A seal member is mounted across the longitudinal opening of the access member and has an internal portion defining an aperture for forming a substantial seal about the surgical object introduced through the longitudinal opening of the access member. The seal member includes a first seal portion extending from the internal portion and being mounted in suspended relation to the access member, and a second seal portion extending from the internal portion and disposed radially outward of the first seal portion, and being attached to the access member.

26 Claims, 4 Drawing Sheets

U.S. PATENT DOCUMENTS

| | | |
|---|---|---|
| 5,871,471 A | 2/1999 | Ryan et al. |
| 5,895,377 A | 4/1999 | Smith et al. |
| 5,989,224 A | 11/1999 | Exline et al. |
| 5,993,471 A | 11/1999 | Riza et al. |
| 6,066,117 A | 5/2000 | Fox et al. |
| 6,093,176 A | 7/2000 | Dennis |
| 6,123,689 A | 9/2000 | To et al. |
| 6,217,555 B1 | 4/2001 | Hart et al. |
| 6,228,061 B1 | 5/2001 | Flatland et al. |
| 6,258,065 B1 | 7/2001 | Dennis et al. |
| 6,482,181 B1 | 11/2002 | Racenet et al. |
| 6,551,282 B1 | 4/2003 | Exline et al. |
| 6,569,119 B1 | 5/2003 | Haberland et al. |
| 6,692,467 B2 | 2/2004 | McFarlane |
| 6,702,787 B2 | 3/2004 | Racenet et al. |
| 6,726,663 B1 | 4/2004 | Dennis |
| 6,923,783 B2 * | 8/2005 | Pasqualucci .................. 604/27 |
| 2002/0107484 A1 | 8/2002 | Dennis et al. |
| 2003/0004529 A1 | 1/2003 | Tsonton et al. |
| 2004/0064100 A1 | 4/2004 | Smith |
| 2004/0106942 A1 | 6/2004 | Taylor et al. |

* cited by examiner

INTRODUCER ASSEMBLY WITH SUSPENDED SEAL

CROSS REFERENCE TO RELATED APPLICATIONS

This application claims priority to U.S. provisional application Ser. No. 60/590,176, filed on Jul. 21, 2004, the entire contents of which are incorporated herein by reference.

BACKGROUND

1. Technical Field

The present disclosure relates to a valve system adapted to permit the introduction of surgical instrumentation into a patient's body. In particular, the present disclosure relates to a valve system for use with an access device which is intended for insertion into a patient's body, and to receive an instrument in sealing engagement therewith.

2. Description of the Related Art

Minimally invasive and laparoscopic procedures generally require that any instrumentation inserted into the body is sealed, i.e., provisions must be made to ensure that gases and/or fluids do not enter or exit the body through an endoscopic incision, such as, for example in surgical procedures where the surgical region is insufflated. For such procedures, the introduction of a tube into anatomical cavities, such as the peritoneal cavity, is usually accomplished by use of a system incorporating a trocar and cannula assembly. Since the cannula is in direct communication with the interior of the peritoneal cavity, insertion of the cannula into an opening in the patient's body to reach the inner abdominal cavity should be adapted to maintain a fluid tight interface between the abdominal cavity and the outside atmosphere. In view of the need to maintain the atmosphere integrity of the inner area of the cavity, a seal assembly for a cannula, which permits introduction of a wide range of surgical instrumentation and maintains the atmospheric integrity of the inner area of the cavity, is desirable. In this regard, there have been a number of attempts in the prior art to achieve such sealing requirements. A difficulty encountered with conventional seal assemblies, however, is the inability of accommodating the wide range of sizes of instrumentation. In addition, manipulation of instrumentation within the cannula often presents difficulties with respect to maintaining seal integrity.

SUMMARY

Accordingly, the present disclosure provides a seal assembly for an access apparatus, which will allow a surgeon to efficaciously utilize instruments of varying diameter in a surgical procedure. This seal assembly obviates the need for multiple adapters to accommodate instruments of varying diameters by providing a resilient seal member which is mounted in a suspended manner to thereby facilitate insertion and withdrawal of the instrument within an aperture of the seal member.

In one preferred embodiment, a surgical access apparatus includes an access member dimensioned for insertion within tissue and having a longitudinal opening to permit introduction of a surgical instrument through the access member to perform a procedure on underlying tissue. A seal member is mounted within the access member. The seal member has a distal seal end which is attached to the access member and a proximal seal end. The proximal seal end is longitudinally movable within the access member upon passage of the surgical instrument through the seal member. The seal member preferably has an inner area that defines an aperture disposed between the proximal seal end and the distal seal end for receiving the surgical instrument in substantial sealed relation therewith. The inner area is adapted to be radially displaced to expand the aperture as the surgical instrument is introduced.

In one preferred embodiment, the proximal seal end of the seal member is disposed radially inwardly of the distal seal end. The distal seal end is connected to the access member along an outer periphery of the distal seal end. Preferably, the proximal seal end defines an outer periphery and an annular member mounted adjacent the outer periphery. The annular member defines a dimension greater than a corresponding dimension of the longitudinal opening of the access member to minimize inversion of the seal member upon withdrawal of the surgical instrument from the seal member.

The proximal seal end may define a general frusto-conical shape. In the alternative, the proximal seal end includes an undulating portion dimensioned to facilitate passage and/or manipulation of the surgical instrument. The distal seal end defines a general hemispherical shape. In a further alternative, the seal member comprises a cylindrical member folded so that the proximal seal end is disposed within the distal seal end.

In accordance with another preferred embodiment, a surgical cannula apparatus is disclosed. The cannula apparatus includes a cannula housing, a cannula sleeve extending from the cannula housing and having a longitudinal opening to permit introduction of a surgical instrument and a seal member mounted relative to the cannula housing. The seal member includes a distal seal end, a proximal seal end disposed within the distal seal end, and an inner area interconnecting the proximal and distal seal ends. The inner area defines an aperture for reception of the surgical instrument in substantial sealed relation therewith. The proximal seal end defines an outer periphery adapted for movement relative to the longitudinal axis. The distal seal end defines an outer periphery which is connected to the cannula housing.

The proximal seal end of the seal member may define a general tapered configuration, e.g., a general frusto-conical configuration. Alternatively, the proximal seal end includes at least one undulation adapted to facilitate movement of the surgical instrument relative to the longitudinal axis.

The distal seal end of the seal member is dimensioned to extend in a general proximal direction from the inner area. Preferably, the distal seal end is dimensioned to extend in a general proximal direction having longitudinal and radial components of direction. In one embodiment, the distal seal end is generally hemispherical in shape.

The proximal seal end may include an annular element associated with the outer periphery thereof. The annular element is preferably less compliant than remaining portions of the inner area of the seal member. The cannula housing may include a transverse wall defining an aperture in general alignment with the axis of the cannula sleeve and being disposed proximal of the seal member. The annular element defines a transverse dimension greater than a corresponding transverse dimension of the aperture of the cannula housing such that the annular element is retained distal of the transverse wall during insertion and withdrawal of the surgical instrument thereby minimizing inversion of the seal member.

In another preferred embodiment, a surgical access apparatus includes an access member dimensioned for insertion within tissue and having a longitudinal opening to permit introduction of a surgical object through the access member to perform a procedure on underlying tissue. A seal member is mounted across the longitudinal opening of the access member and has an internal portion defining an aperture for forming a substantial seal about the surgical object introduced through the longitudinal opening of the access member. The seal member includes a first seal portion extending from the internal portion and being mounted in suspended relation to the access member, and a second seal portion extending from the internal portion and disposed radially outward of the first seal portion, and being attached to the access member.

A method of providing a seal around a surgical instrument is also disclosed. The method includes the steps of:

providing a cannula assembly including an access housing defining a longitudinal axis and a seal having a distal end that is attached to the access housing and a proximal end that is longitudinally movable with respect to the distal end;

engaging the proximal end with the surgical instrument; and moving the proximal end longitudinally with respect to the distal end so that the seal unfolds.

BRIEF DESCRIPTION OF THE DRAWINGS

The foregoing features of the present disclosure will become more readily apparent and will be better understood by referring to the following detailed description of preferred embodiments, which are described hereinbelow with reference to the drawings wherein.

DETAILED DESCRIPTION OF PREFERRED EMBODIMENTS

The seal assembly of the present disclosure, either alone or in combination with a seal system internal to a cannula assembly, provides a substantial seal between a body cavity of a patient and the outside atmosphere before, during and after insertion of an instrument through the cannula assembly. Moreover, the seal assembly of the present disclosure is capable of accommodating instruments of varying diameters, e.g., from 5 mm to 15 mm, by providing a gas tight seal with each instrument when inserted. The flexibility of the present seal assembly facilitates endoscopic surgery where a variety of instruments having different diameters are often needed during a single surgical procedure.

The seal assembly contemplates the introduction and manipulation of various types of instrumentation adapted for insertion through a trocar and/or cannula assembly while maintaining a fluid tight interface about the instrumentation to preserve the atmospheric integrity of a surgical procedure from gas and/or fluid leakage. Examples of instrumentation include clip appliers, graspers, dissectors, retractors, staplers, laser probes, photographic devices, endoscopes and laparoscopes, tubes, and the like. Such instruments will be collectively referred to herein as "instruments or instrumentation". Alternatively, the seal assembly may be incorporated in a hand access device. A hand access device contemplates the introduction of a hand through the device to assist in performing the surgery. Such hand assisted surgery may be performed in a pressurized environment, e.g., an insufflated abdominal cavity.

In the following description, as is traditional, the term "proximal" refers to the end of the instrument closest to the operator while the term "distal" refers to the end of the instrument remote from the operator.

Figure 1:
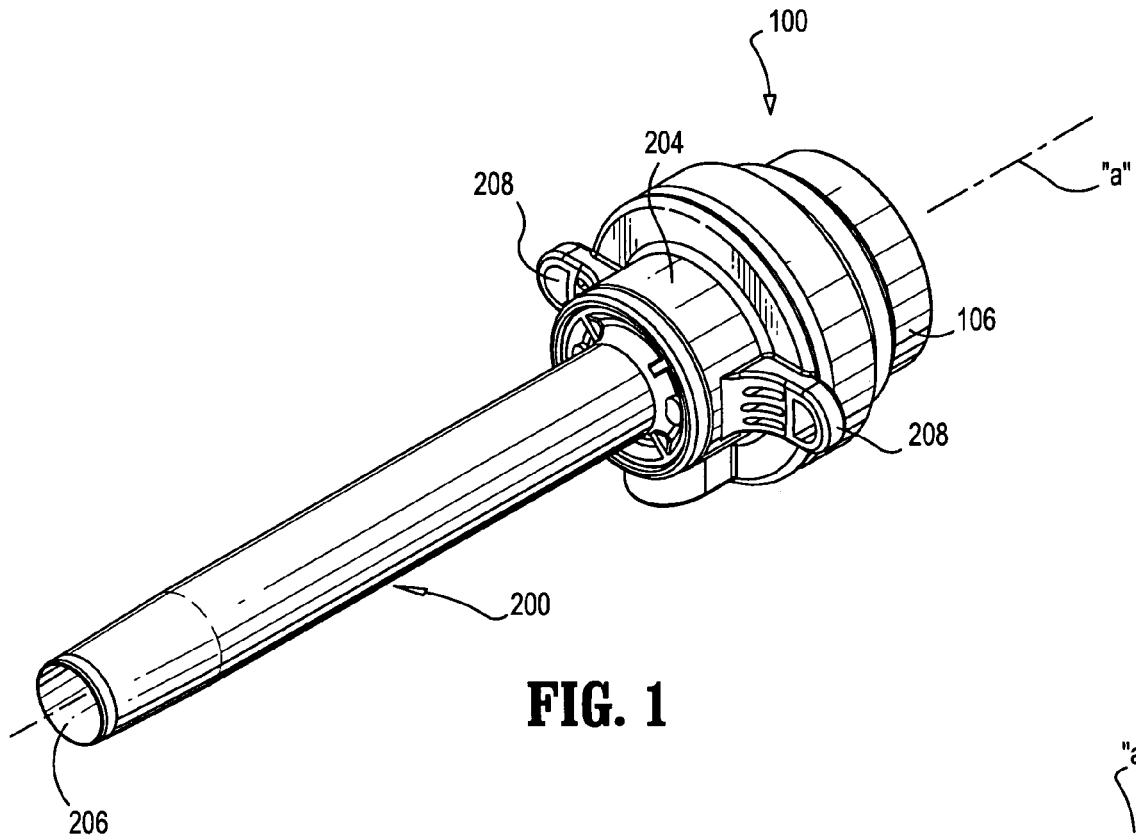
FIGS. 1-2 are perspective views of a cannula assembly and a seal assembly in accordance with the principles of the present disclosure.
Figure 2:
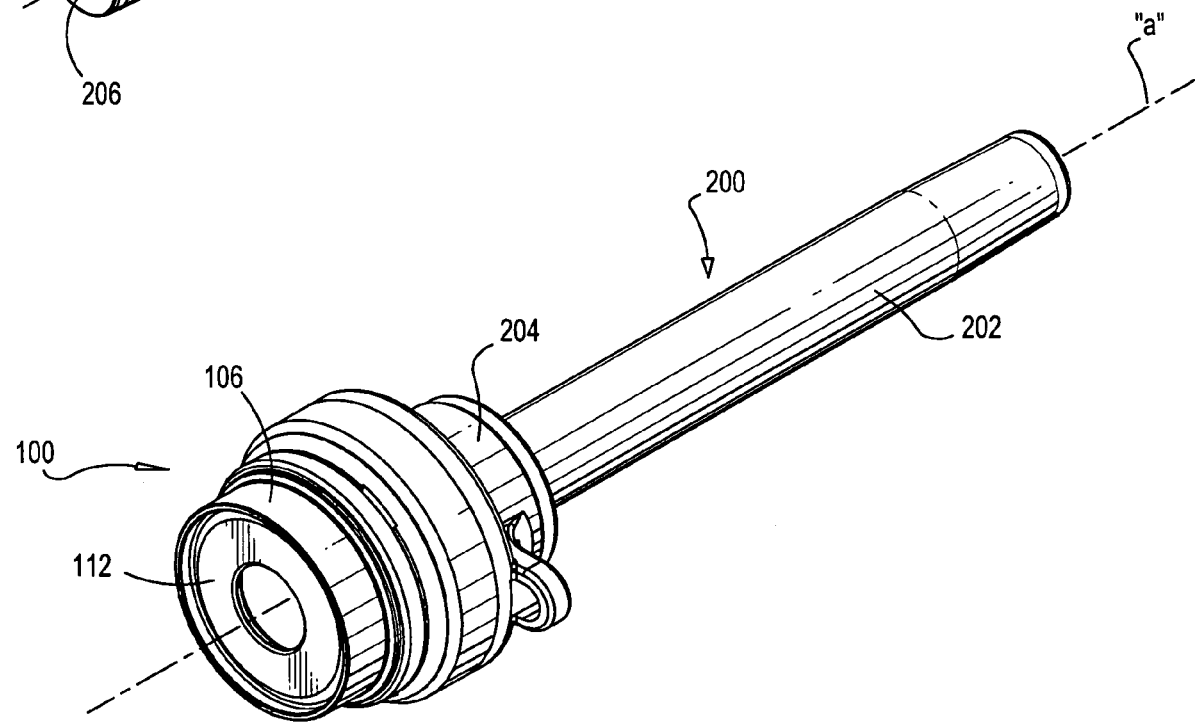

Referring now to the drawings, in which like reference numerals identify identical or substantially similar parts throughout the several views, FIGS. 1-2 illustrate the seal assembly 100 of the present disclosure mounted to cannula assembly 200. Cannula assembly 200 may be any conventional cannula suitable for the intended purpose of accessing a body cavity and permit introduction of instruments therethrough. For example, cannula assembly may be similar to the system disclosed in commonly assigned U.S. patent application Ser. No. 10/264,556, filed Oct. 4, 2002, the contents of such disclosure being incorporated by its entirety herein. Cannula assembly 200 is particularly adapted for use in laparoscopic surgery where the peritoneal cavity is insufflated with a suitable gas, e.g., $CO_2$, to raise the cavity wall from the internal organs therein. Cannula assembly 200 is typically used with an obturator assembly (not shown) which is a sharp pointed instrument positionable within the passageway of the cannula assembly 200. The obturator assembly is utilized to penetrate the abdominal wall and then subsequently removed from the cannula assembly to permit introduction of the surgical instrumentation utilized to perform the procedure.

Cannula assembly 200 includes cannula sleeve 202 and cannula housing 204 mounted to an end of the sleeve 202. Cannula sleeve 202 defines a longitudinal axis "a" extending along the length of sleeve 202. Sleeve 202 further defines an internal longitudinal passage 206 dimensioned to permit passage of surgical instrumentation.

Cannula housing 204 may be a multi-component element secured via a snap fit, ultrasonic welding or any other means envisioned by one skilled in the art including, e.g., adhesive means. Cannula housing 204 may further include diametrically opposed housing grips 208 dimensioned and arranged for gripping engagement by the fingers of the user.

Cannula housing 204 may further include an internal duck bill or zero closure valve (not shown). Such valve opens to permit passage of the surgical instrumentation and closes in the absence of the instrumentation. The valve may be preferably adapted to close upon exposure to the forces exerted by the insufflation gases in the internal cavity. Other zero closure valves are also contemplated including singer or multiple slit valve arrangements, trumpet valves, flapper valves, etc.

Cannula sleeve 202 and cannula housing 204 may be formed of stainless steel or other rigid materials such as a polymeric material or the like. Cannula sleeve 202 and/or cannula housing 204 may be clear or opaque. The diameter of sleeve 202 may vary, but typically ranges from 10 to 15 mm to accommodate a range of instrument sizes.

Referring now the FIG. 3, in conjunction with FIGS. 1-2, seal assembly 100 will be discussed in detail. Seal assembly 100 includes seal housing, generally identified as reference numeral 102, and seal 104 disposed within the seal housing 102 in suspended relation therewith. Seal housing 102 houses the sealing components of the assembly and defines central seal housing axis "b" which is preferably parallel to the axis "a" of cannula sleeve 202 and, more specifically, coincident with the axis "a" of the cannula when the seal assembly 100 is mounted to the cannula assembly 100. In one embodiment, seal housing 102 incorporates two housing components, namely, upper and lower housing components 106, 108, respectively, which, when assembled together, form the seal housing 102. Assembly of housing components 106, 108 may be affected by any of the aforementioned connection means discussed with respect to cannula housing 204. Alternatively, seal housing 102 may be monolithically formed as a single unit.

Upper housing component 106 defines outer wall 110 and transverse planar wall 112 disposed between the ends of the outer wall 110. Transverse planar wall 112 defines central aperture 114 which is preferably coaxially arranged relative to housing axis "b". Central aperture 114 defines a diameter sufficient to accommodate the largest-diameter instrument contemplated for insertion within seal housing 102. Transverse planar wall 112 defines an annular recess 116 in its lower surface disposed about central aperture 114.

Lower housing component 108 includes inner wall 118 depending upwardly from transverse base 120 of the lower housing component 108, and first and second outer walls 122,124 arranged to depend downwardly relative to the base 120. Inner wall 118 is preferably correspondingly dimensioned to be received within outer wall 110 of upper housing component 106 and form an interference or friction fit to mount upper and lower housing components 106, 108. Similarly, first outer wall 122 of lower housing component 108 may receive a wall of cannula housing 204 and form a friction fit to secure seal housing 102 to cannula housing 204. Other means to mount seal housing 102 and cannula housing 204 are envisioned including a bayonet lock, snap fit, adhesives etc. Lower housing component 108 further includes internal tapered wall 126 extending from base 120 and tapering radially inwardly relative to seal housing axis "b".

Figure 3:
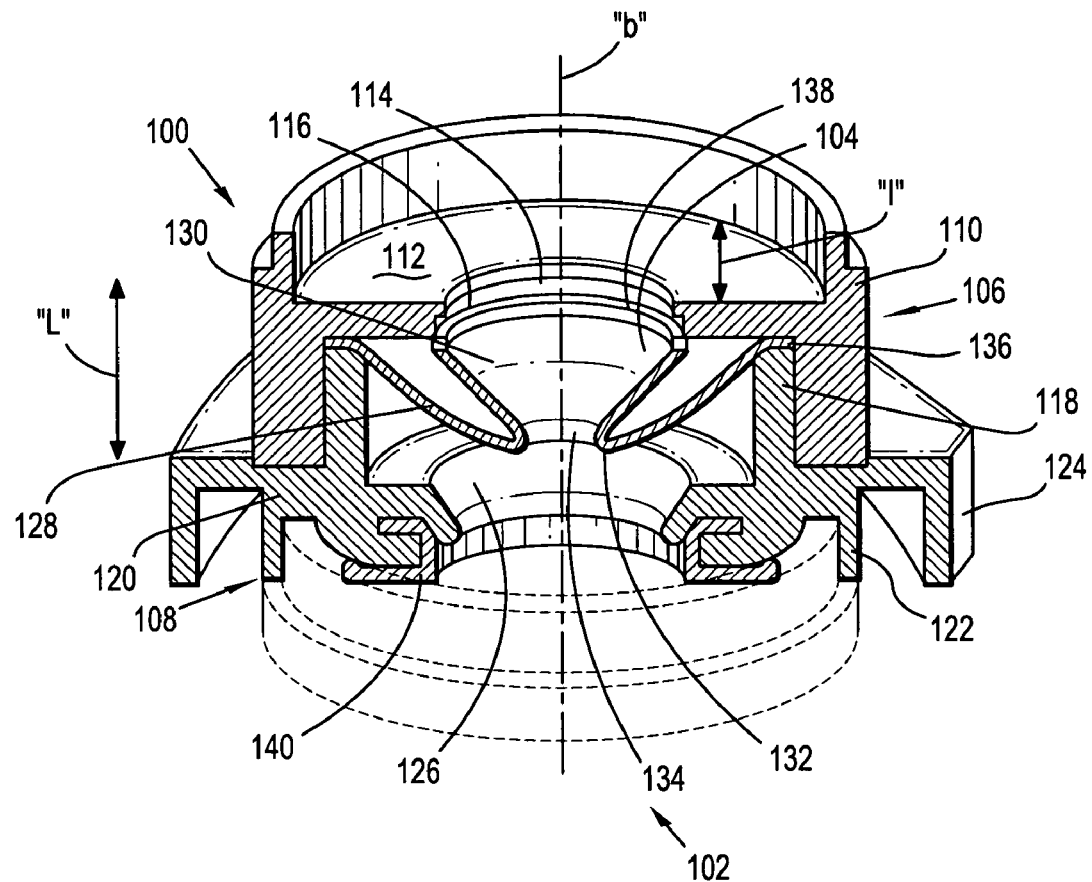
FIG. 3 is a side cross-sectional view of the seal assembly in accordance with the embodiment of FIGS. 1-2.
Figure 4:
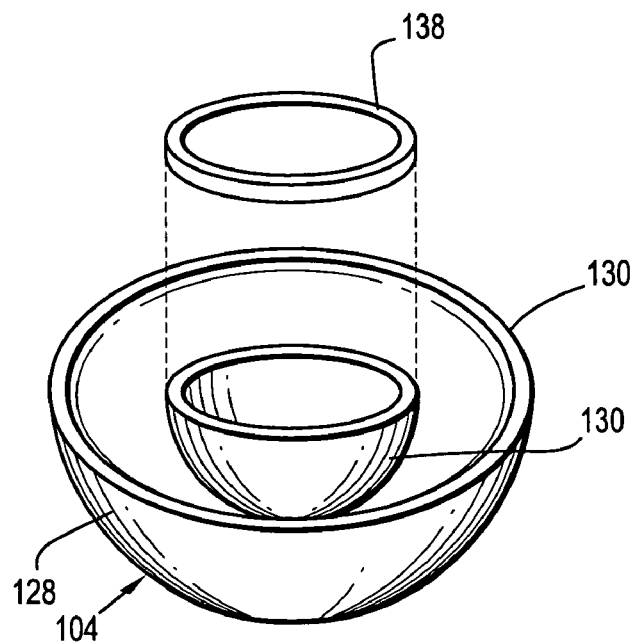
FIG. 4 is a perspective view of the seal of the seal assembly in accordance with the embodiment of FIGS. 1-3.

With reference now to FIGS. 3-4, suspended seal 104 includes outer or distal seal end 128 and inner or proximal seal end 130 disposed at least partially within the distal seal end 128. Suspended seal 104 defines internal seal area 132 (FIG. 3) which connects distal and proximal seal ends 128, 130 and defines central seal aperture 134. Distal seal end 128 defines an outer peripheral flange 136. Outer flange 136 is trapped between planar wall 112 of upper housing component 106 and inner wall 118 of lower housing component 108 to mount seal 104 within seal housing 102 in a suspended manner. Distal seal end 128 extends radially inwardly from outer flange 136 to internal seal area 132 of seal 104. More specifically, distal seal end 128 has both a transverse and longitudinal component of direction and preferably defines an arcuate, hemispherical or bell shape as shown. Distal seal end 128 may have any elongated configuration including frusto-conical, hourglass, etc. Seal 104 is desirably shaped to form seal aperture 134 which is dimensioned less than the diameter of the instrument, or smallest of the range of instrument sizes to be used with cannula assembly 200.

Proximal seal end 130 extends upwardly from internal seal area 132 where it terminates in washer 138. Proximal seal end 130 is shown as being generally frusto-conical in shape. However, proximal seal end 124 may assume any other configuration including hemispherical, bell shaped, hourglass, etc., i.e., proximal seal end 130 has both a transverse end longitudinal component of direction. Proximal seal end 130 may be a planar or disc-shaped seal.

Washer 138 is embedded or connected to the upper end of proximal seal end 128. Attachment of washer 138 to the upper end may be effected by any means including adhesives, cements or the like. Alternatively, washer 138 may be molded within seal 104 to be embedded within proximal seal end 130 during manufacture of the seal 104. Washer 138 is movably disposed within seal housing 102 and is desirably not attached or connected to upper housing component 106 or any other structure of seal housing 102. Accordingly, washer 138 and proximal seal end 130 may move in a longitudinal direction "L" (FIG. 3) either toward or away from cannula sleeve 202 during respective introduction or removal of the instrument. This movement of washer 138 facilitates the insertion and removal of the surgical instrument. The diameter of washer 138 preferably approximates, or is greater than, the inner diameter of central aperture 114 of planar wall 112. Through this dimensioning, washer 138 is prevented from passing through central aperture 114 during withdrawal of the instrument thus preventing inversion of seal 104. Washer 138 is accommodated within annular recess 116 of transverse planar wall 112 of upper housing component 106 when in an initial condition shown in FIG. 3. Washer 138 is preferably formed of a material less compliant than seal member 102 and may be a rigid polymeric material or metallic material.

Seal 104 of seal assembly 100 preferably comprises a resilient material in at least the region of internal seal area 130 to form a substantial seal about an instrument inserted through seal aperture 134. Seal 104 may be monolithically formed or composed of several components interconnected to each other. In one preferred embodiment, seal 104 comprises an elastomeric material, which may comprise, e.g., a silicon rubber. In another embodiment, seal 104 includes a resilient elastomer (e.g., polyisoprene or natural rubber) and has a layer of fabric impregnated on each surface of the resilient seal 104. The fabric may be of any suitable fabric for example, a SPANDEX material containing about 20% LYCRA and about 80% NYLON available from Milliken. A suitable seal member or seal type is disclosed in commonly assigned U.S. Pat. No. 6,702,787 to Racenet et al. and/or U.S. Pat. No. 6,482,181 to Racenet et al., the entire contents of each disclosure being incorporated herein by reference.

Although seal 104 is disclosed as an impregnated fabric arrangement, it is appreciated that other seal types may be used and still achieve the objectives of the present disclosure. For example, seal 104 may be fabricated from an elastomeric material without the embedded fabric. Gel, foams, or other fluid-filled bladder seal arrangements are also envisioned.

Seal housing 102 further includes a second seal 140 at least partially received within channel 142 of lower housing component 108. Second seal 140 engages cannula housing 204 upon mounting of seal housing 102 to the cannula housing 204 to form a substantial seal at this interface thereby substantially eliminating undesired passage of insufflation gas at this interface.

Figure 5:
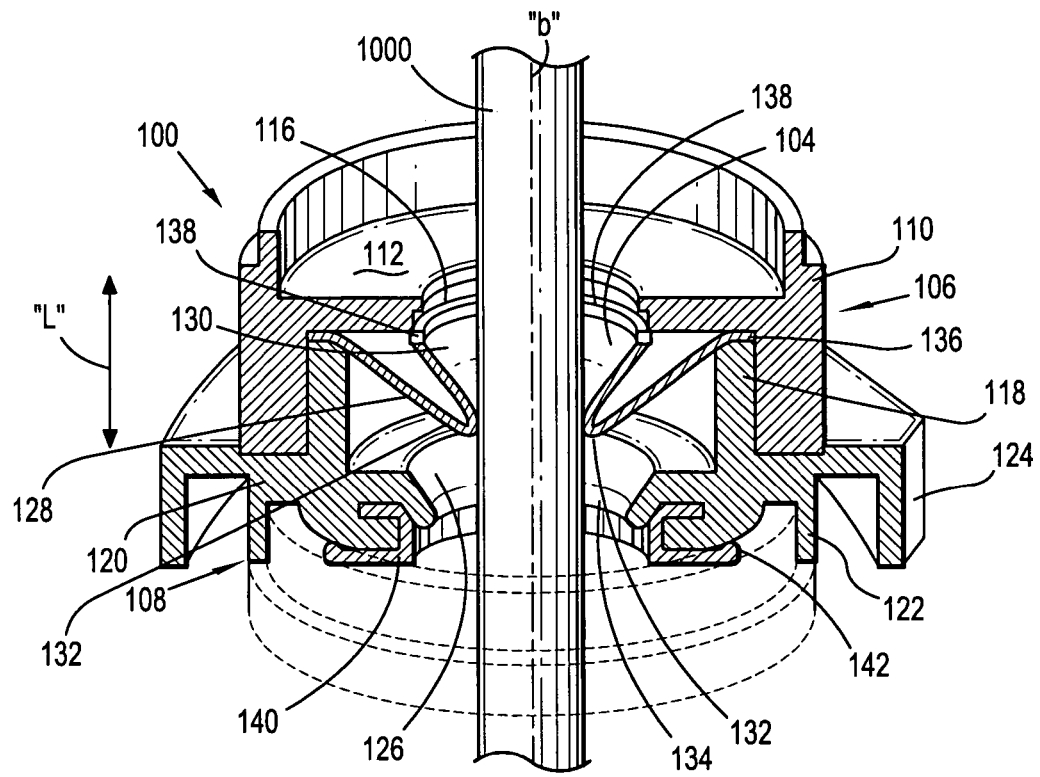
FIG. 5 is a side cross-sectional view of the seal assembly in accordance with the embodiment of FIG. 4 illustrating insertion of a surgical instrument within the seal assembly.
Figure 6:
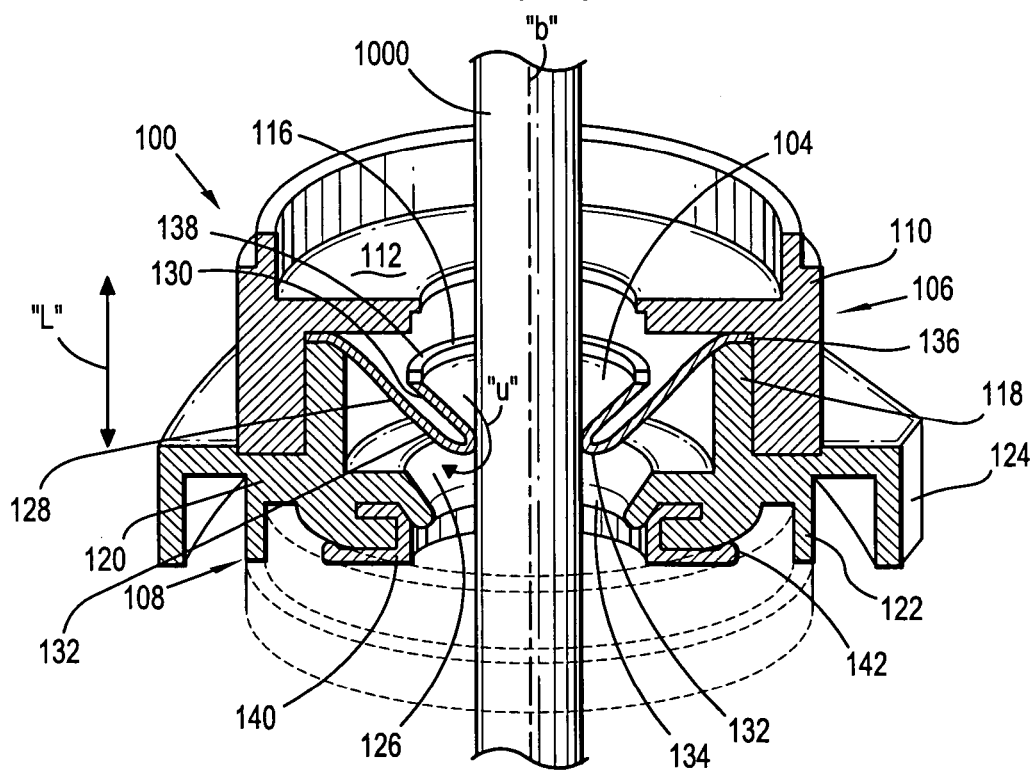
FIG. 6 is a side cross-sectional view of the seal assembly in accordance with the embodiment of FIG. 5 illustrating insertion of a surgical instrument within the seal assembly.

The use of the seal assembly 100 and cannula assembly 200 in connection with introduction of a surgical instrument will be discussed. Seal assembly 100 is mounted to cannula assembly 200 which is previously introduced into an insufflated abdominal cavity. An instrument 1000 is inserted into seal assembly 100 through aperture 114 of seal housing 102. As best depicted in FIG. 5, the instrument 1000 engages proximal seal end 130. As best depicted in FIG. 6, the force applied by the instrument causes proximal seal end 130 and, possibly, to some extent, distal seal end 128, to be displaced toward cannula sleeve 202. During this movement, washer 138, which can move in the distal direction, may also move downwardly in a longitudinal direction within seal housing 102. As indicated by the directional arrow "U" in FIG. 6, seal 104 unrolls as proximal seal end 130 moves within seal housing 102 to accommodate the instrument. In so doing, aperture 134 enlarges. In addition, internal seal area 132, which defines central seal aperture 134 of seal 104, stretches to accommodate the instrument diameter, as necessary to form a seal about the instrument 1000. The instrument 1000 passes further distally into the cannula housing 204 passing through the duckbill valve (not shown) and cannula sleeve 202 into the body cavity. The surgeon performs the desired operation procedure. After the surgery is completed, the surgeon withdraws the instrument. During withdrawal of the instrument, seal 104 is prevented from inverting due to engagement of washer 138 with planar wall 112.

Figure 7:
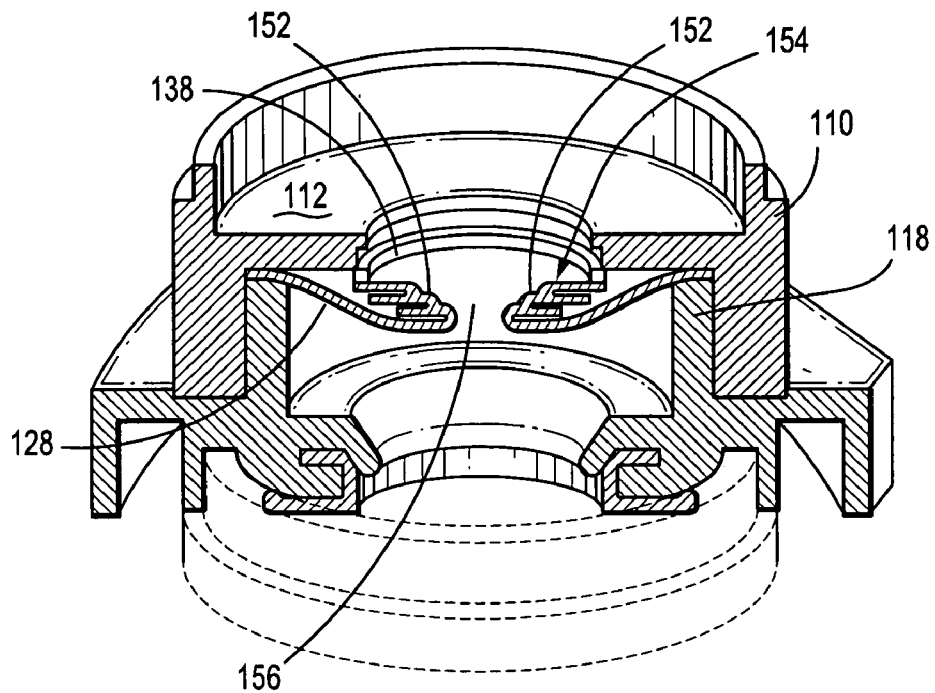
FIG. 7 is a side cross-sectional view of an alternate embodiment of the seal assembly.
Figure 8:
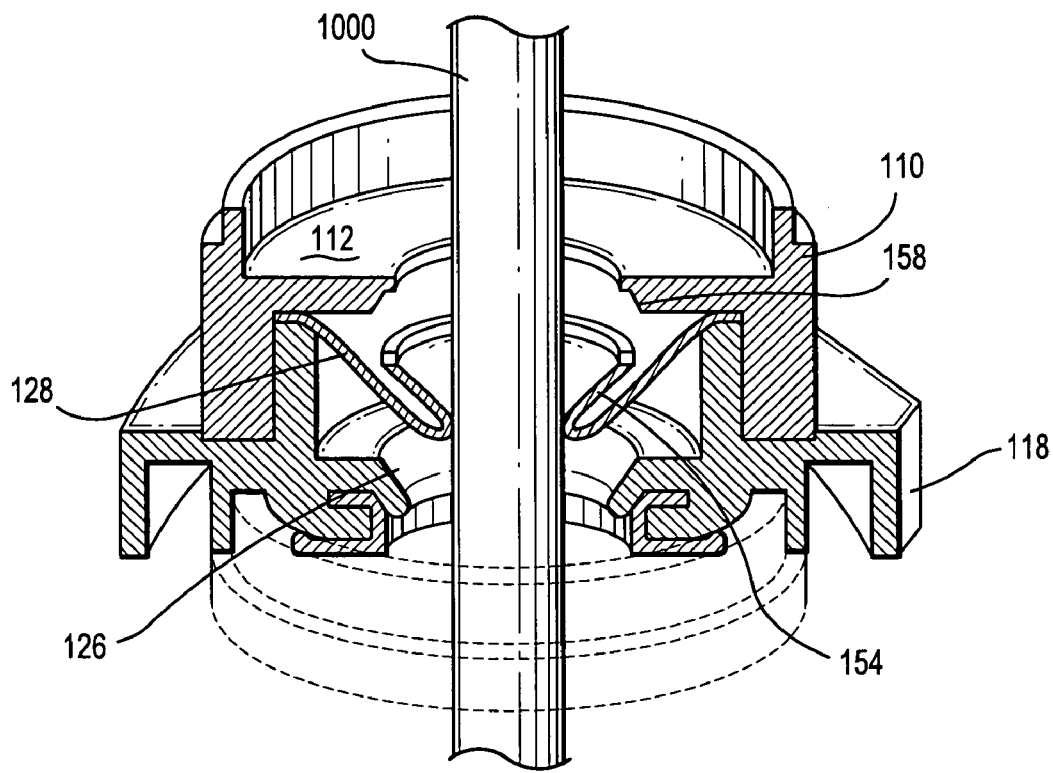
FIG. 8 is a side cross-sectional view of the seal assembly in accordance with the embodiment of FIG. 7 illustrating insertion of a surgical instrument within the seal assembly.

FIG. 7 illustrates an alternate embodiment of the present disclosure. This embodiment is substantially similar to the embodiment of FIG. 3; however, with this embodiment, seal 150, at an at rest or initial position, defines a plurality of folds 152 within at least proximal seal end 154 as depicted in FIG. 7. Accordingly, these folds 152 unravel or roll during introduction of the instrument to, e.g., assume the arrangement (e.g., relatively linear arrangement) of seal 102 depicted in FIG. 8. The unfolding of proximal seal end 154 significantly enhances passage and manipulation of the instrument within cannula sleeve 102 by e.g., reducing the initial forces necessary to remove the instrument. Likewise, during withdrawal of the instrument, proximal seal end 154 may fold upon itself or roll to return to the configuration of FIG. 7 to facilitate removal of the instrument by reducing the initial forces necessary to remove the instrument through aperture 156 of seal 102. As noted, washer 138 prevents inversion of seal 150 upon withdrawal of the instrument. A further feature of this embodiment is provision of chamfered surface or cut-out 158 on the lower side of planar wall 112. Chamfered surface 158 serves to guide washer 138 into alignment with the seal axis "b" during removal of the instrument. As a further alternative, it is envisioned that washer 138 may be secured to the underside of planar wall 112 whereby only the central areas of proximal and distal seal ends displace in the longitudinal direction during insertion and removal of the instrument.

In a further embodiment, the seal comprises an elastomeric material formed in the shape of a cylinder. The cylindrical seal is folded into the conical shape shown in FIG. 3 and both ends are connected to seal housing 102. The upper end of the cylindrical seal is resiliently attached to seal housing 102 so that the upper end can move longitudinally with respect to the lower end of the seal and so that the seal can unravel or unfold, as discussed above. The upper end of the cylindrical seal may include washer 138, as discussed above. In another embodiment, the upper end of the cylindrical seal is captured within a groove in the seal housing so that the upper end can move longitudinally.

While the invention has been particularly shown and described with reference to the preferred embodiments, it will be understood by those skilled in the art that various modifications and changes in form and detail may be therein without departing from the scope and spirit of the invention. Accordingly, modifications such as those suggested above, but no limited thereto, are to be considered within the scope of the invention.

What is claimed is:

1. A surgical access apparatus, which comprises:
    an access member dimensioned for insertion within tissue, the access member having proximal and distal ends and defining a longitudinal axis, and having a longitudinal opening to permit introduction of a surgical object through the access member to perform a procedure on underlying tissue; and
    a seal member mounted across the longitudinal opening of the access member and having an internal portion defining an aperture for forming a substantial seal about the surgical object introduced through the longitudinal opening of the access member, the seal member including a first seal portion extending from the internal portion in a general proximal longitudinal direction and being mounted in suspended relation to the access member, and a second seal portion connected to the first seal portion by the internal portion such that the second seal portion extends from the internal portion in a general proximal longitudinal direction and is disposed radially outward of the first seal portion, and wherein a proximal end of the first seal portion is configured to move distally in response to distal advancement of the surgical object inserted therethrough.

2. The surgical access apparatus according to claim 1, further comprising a washer disposed adjacent the proximal end of the first seal portion, the washer being dimensioned to help prevent inversion of the seal member during proximal translation of the surgical instrument.

3. A surgical access apparatus, which comprises:
    an access member dimensioned for insertion within tissue, the access member having proximal and distal ends and defining a longitudinal axis, and having a longitudinal opening to permit introduction of a surgical instrument through the access member to perform a procedure on underlying tissue; and
    a seal member comprising an elastomeric material and being mounted across the longitudinal opening of the access member, the seal member including a first outer seal portion having an outer periphery secured relative to the access member, the first outer seal portion extending in at least a distal longitudinal direction to a central seal area, the central seal area defining a seal passage and being configured to engage the surgical instrument such that a substantially fluid tight seal is formed therewith, and a second inner seal portion extending in at least a proximal longitudinal direction from the central seal area such that the central area interconnects the first outer seal portion and the second inner seal portion, the second inner seal portion being at least partially disposed within the first outer seal portion, the second inner seal portion defining an inner seal end suspended relative to the access member whereby a proximal end of the inner seal portion is adapted for longitudinal movement within the longitudinal opening of the access member upon passage or the surgical instrument.

4. The surgical access apparatus according to claim 3, wherein the central seal area is adapted to be radially displaced to expand the seal passage as the surgical instrument is introduced.

5. The surgical access apparatus according to claim 4, wherein the inner seal end of the second inner seal portion is disposed radially inwardly of the outer periphery of the first outer seal portion.

6. The surgical access apparatus according to claim 3 wherein the inner seal end has an annular member mounted thereto.

7. The surgical access apparatus according to claim 6 wherein the annular member defines a dimension greater than a corresponding dimension of the longitudinal opening of the access member to minimize inversion of the seal member upon withdrawal of the surgical instrument from the seal member.

8. The surgical access apparatus according to claim 3 wherein the second inner seal portion defines a general frusto-conical shape.

9. The surgical access apparatus according to claim 3 wherein the second inner seal portion includes an undulating portion dimensioned to facilitate passage and/or manipulation of the surgical instrument.

10. The surgical access apparatus according to claim 3 wherein the first outer seal portion defines a general hemispherical shape.

11. The surgical access apparatus according to claim 3 wherein the seal member is monolithically formed.

12. The surgical access apparatus according to claim 3 wherein the seal member comprises a cylindrical member folded so that the second inner seal portion is disposed within the first outer seal portion.

13. The surgical access apparatus according to claim 3, further comprising a washer disposed adjacent the proximal end of the inner seal portion, the washer being configured to help prevent inversion of the seal member during withdrawal of the surgical instrument.

14. A surgical cannula apparatus, which comprises:
a cannula housing;
a cannula sleeve extending from the cannula housing, the cannula sleeve defining a longitudinal axis and having a longitudinal opening to permit introduction of a surgical instrument; and
a seal member mounted relative to the cannula housing, the seal member including an elongated outer seal portion, an elongated inner seal portion, and an inner fold area interconnecting the outer seal portion and the inner seal portion whereby the seal member is at least partially inverted such that the inner seal portion is at least partially disposed within the outer seal portion, the inner fold area defining an aperture for reception of the surgical instrument in substantial sealed relation therewith, the inner seal portion including a proximal end displaced from the fold area, the proximal end of the inner seal portion being adapted for movement relative to the longitudinal axis, the outer seal portion defining an outer periphery connected to the cannula housing.

15. The surgical cannula apparatus according to claim 14 wherein the inner seal portion defines a general tapered configuration.

16. The surgical cannula apparatus according to claim 14 wherein the inner seal portion includes at least one undulation adapted to facilitate movement of the surgical instrument relative to the longitudinal axis.

17. The surgical cannula apparatus according to claim 14 wherein the inner seal portion defines a general frusto-conical configuration.

18. The surgical cannula apparatus according to claim 14 wherein the outer seal portion is dimensioned to extend in a general proximal direction from the inner area.

19. The surgical cannula apparatus according to claim 18 wherein the outer seal portion is dimensioned to extend in a general proximal direction having longitudinal and radial components of direction.

20. The surgical cannula apparatus according to claim 14 wherein the outer seal portion is generally hemispherical in shape.

21. The surgical cannula apparatus according to claim 14 wherein the inner seal portion includes an annular element associated with the outer periphery thereof the annular element being less compliant than remaining portions of the inner area.

22. The surgical cannula apparatus according to claim 21 wherein the cannula housing includes a transverse wall defining an aperture in general alignment with the axis of the cannula sleeve and being disposed proximal of the seal member.

23. The surgical cannula apparatus according to claim 21 wherein the annular element defines a transverse dimension greater than a corresponding transverse dimension of the aperture of the cannula housing such that the annular element is retained distal of the transverse wall during insertion and withdrawal of the surgical instrument thereby minimizing inversion of the seal member.

24. The surgical cannula apparatus according to claim 14 wherein the seal member comprises an elastomeric material.

25. The surgical cannula apparatus according to claim 14 wherein the seal end of the inner seal portion is suspended relative to the access member.

26. The surgical cannula apparatus according to claim 14, further comprising a washer disposed adjacent the proximal end of the inner seal portion, the washer being dimensioned to help prevent inversion of the seal member during proximal translation of the surgical instrument.

* * * * *